US008655486B2

(12) United States Patent  (10) Patent No.: US 8,655,486 B2
Sanders et al.  (45) Date of Patent: Feb. 18, 2014

(54) SYSTEMS AND METHODS FOR MANAGING MEDICATION-DISPENSING CANISTERS

(75) Inventors: Ron Sanders, Spokane, WA (US);
Harpreet Singh, Everett, WA (US);
Frank Mckeown, Carnation, WA (US);
Paul Richardson, Redmond, WA (US);
John M. Manning, Seattle, WA (US);
Darcy O. Clarke, Kent, WA (US)

(73) Assignee: Talyst Inc., Kirkland, WA (US)

( * ) Notice: Subject to any disclaimer, the term of this patent is extended or adjusted under 35 U.S.C. 154(b) by 293 days.

(21) Appl. No.: 13/298,172

(22) Filed: Nov. 16, 2011

(65) Prior Publication Data

US 2013/0123977 A1   May 16, 2013

(51) Int. Cl.
*G06F 17/00* (2006.01)
*G06Q 50/00* (2012.01)

(52) U.S. Cl.
USPC ................ 700/242; 700/231; 221/241; 705/2

(58) Field of Classification Search
USPC ........ 705/2; 221/241; 700/231, 232, 241, 242
See application file for complete search history.

(56) References Cited

U.S. PATENT DOCUMENTS

| 5,897,024 | A | * | 4/1999 | Coughlin et al. | 221/241 |
| 6,611,733 | B1 | * | 8/2003 | De La Huerga | 700/242 |
| 7,014,063 | B2 | * | 3/2006 | Shows et al. | 221/211 |
| 7,735,683 | B2 | * | 6/2010 | Handfield et al. | 221/241 |
| 2011/0251850 | A1 | | 10/2011 | Stephens | |

OTHER PUBLICATIONS

International Search Report and Written Opinion mailed Mar. 21, 2013, issued in corresponding International Application No. PCT/US2012/064747, filed Nov. 13, 2012, 11 pages.

* cited by examiner

*Primary Examiner* — Timothy Waggoner
(74) *Attorney, Agent, or Firm* — Christensen O'Connor Johnson Kindness PLLC

(57) ABSTRACT

Systems and methods for managing canisters used to automatically dispense medication are provided. Canisters are configurable via a design process and a build process to accurately dispense a variety of medications. Design profiles are created and stored by a canister management system, and are federated to workstations used to build and fill the canisters, and to workstations used to dispense the medication. Information related to the build process, the fill process, and the dispense process is also federated by the system. The system also enables the transmission of other types of messages between client applications on the workstations and the canister management system. The system is useful to federate data regardless of a structure of a supply chain used to design, build, distribute, and use the canisters.

20 Claims, 11 Drawing Sheets

SYSTEMS AND METHODS FOR MANAGING MEDICATION-DISPENSING CANISTERS

BACKGROUND

Systems for automating pharmacy operations are useful for reducing the cost of running a pharmacy. For example, a canister that automatically counts medication for dispensing eliminates the need for a pharmacist or technician to manually count individual pills when filling a prescription. However, such canisters are generally configured for a given medication. Obtaining new canisters for each new medication can be costly, and experimenting with existing containers to determine an appropriate canister for a new medication can be time-consuming and difficult. With the advent of large-scale pharmacies serving sizeable populations, such as nursing homes, long-term care facilities, and/or the like, the problems of dealing with many types of medication and managing canister configurations are exacerbated even further.

What is needed are systems and methods for dispensing a large variety of changing medications in a more efficient and cost-effective manner.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-readable medium having computer-executable instructions stored thereon is provided. The computer-executable instructions, if executed by one or more processors of a computing device, cause the computing device to perform actions for managing canister data, the actions comprising storing a design profile that includes configuration settings usable to configure a canister to dispense a medication; storing a build profile that includes information associated with a canister built based on the design profile; and storing a fill profile that includes information associated with filling the canister with the medication.

In some embodiments, a system comprising a canister management system, a canister messaging system communicatively coupled to the canister management system, and one or more canister workstations is provided. The canister management system includes one or more master profile data stores and a canister data engine communicatively coupled to the plurality of master profile data stores. The canister messaging system includes one or more local profile data stores and a canister messaging engine communicatively coupled to the canister data engine and the one or more local profile data stores. The one or more canister workstations are configured to request profile information associated with a canister from the canister data engine or the canister messaging engine, and submit new profile information to the canister data engine or the canister messaging engine.

In some embodiments, a method for dispensing a medication from a configurable canister is provided. One or more canister configuration settings suitable to configure a canister to dispense the medication are determined. The canister configuration settings are stored in a design profile. A canister is built based on the design profile. Information related to the building of the canister is stored in a build profile. The canister is filled with the medication, information is stored related to the filling of the canister in a fill profile, and the medication is dispensed using the canister.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The present disclosure describes examples of systems and methods for managing configurable medication-dispensing canisters. The canisters may comprise configurable parts that can be reconfigured to accept and dispense different medications. Data representing canister design, build, fill, and dispensing actions, among others, can be managed by a centralized system, and is federated to workstations as appropriate for performing actions relating to the canisters.

Figure 1A:
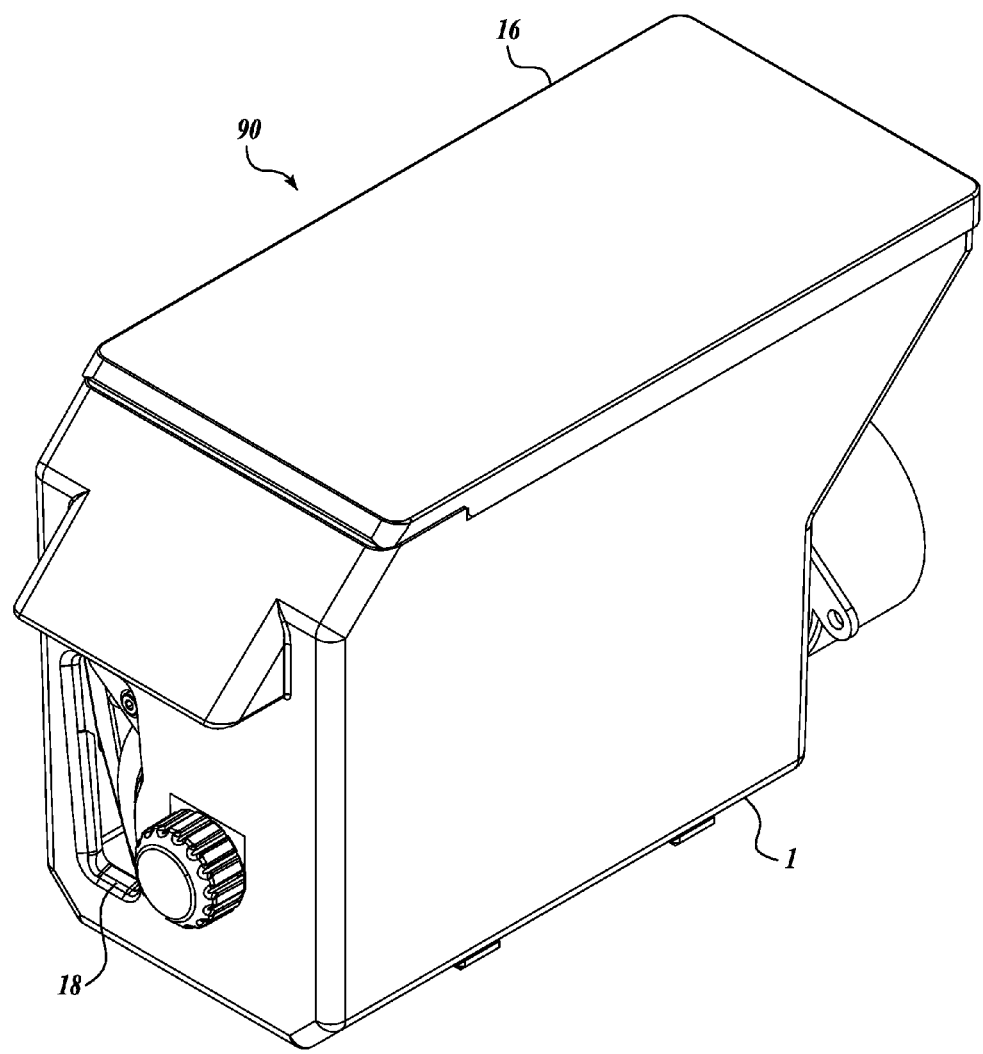
FIG. 1A is a top isometric view of an exemplary canister for use with embodiments of the present disclosure.
Figure 1B:
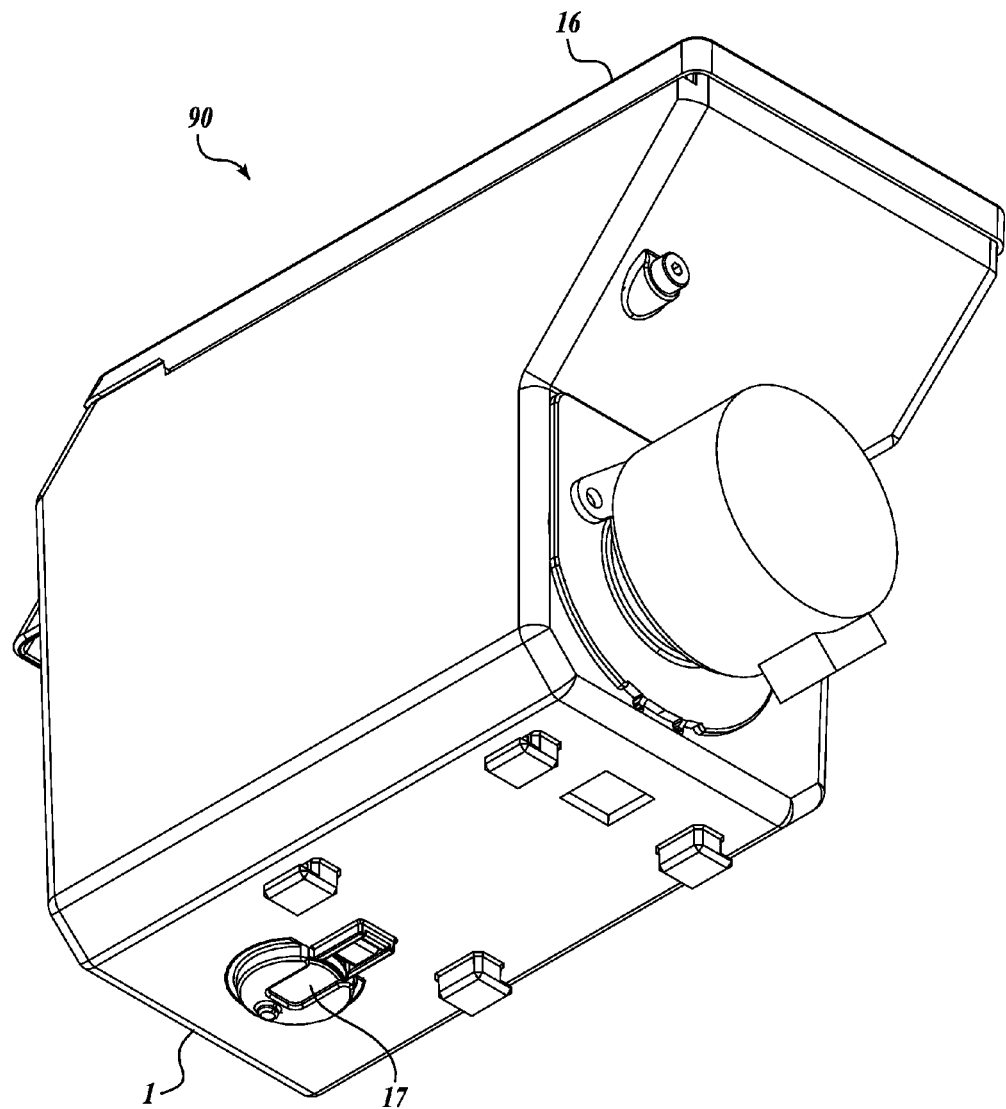
FIG. 1B is a bottom isometric view of the exemplary canister of FIG. 1A.
Figure 2:
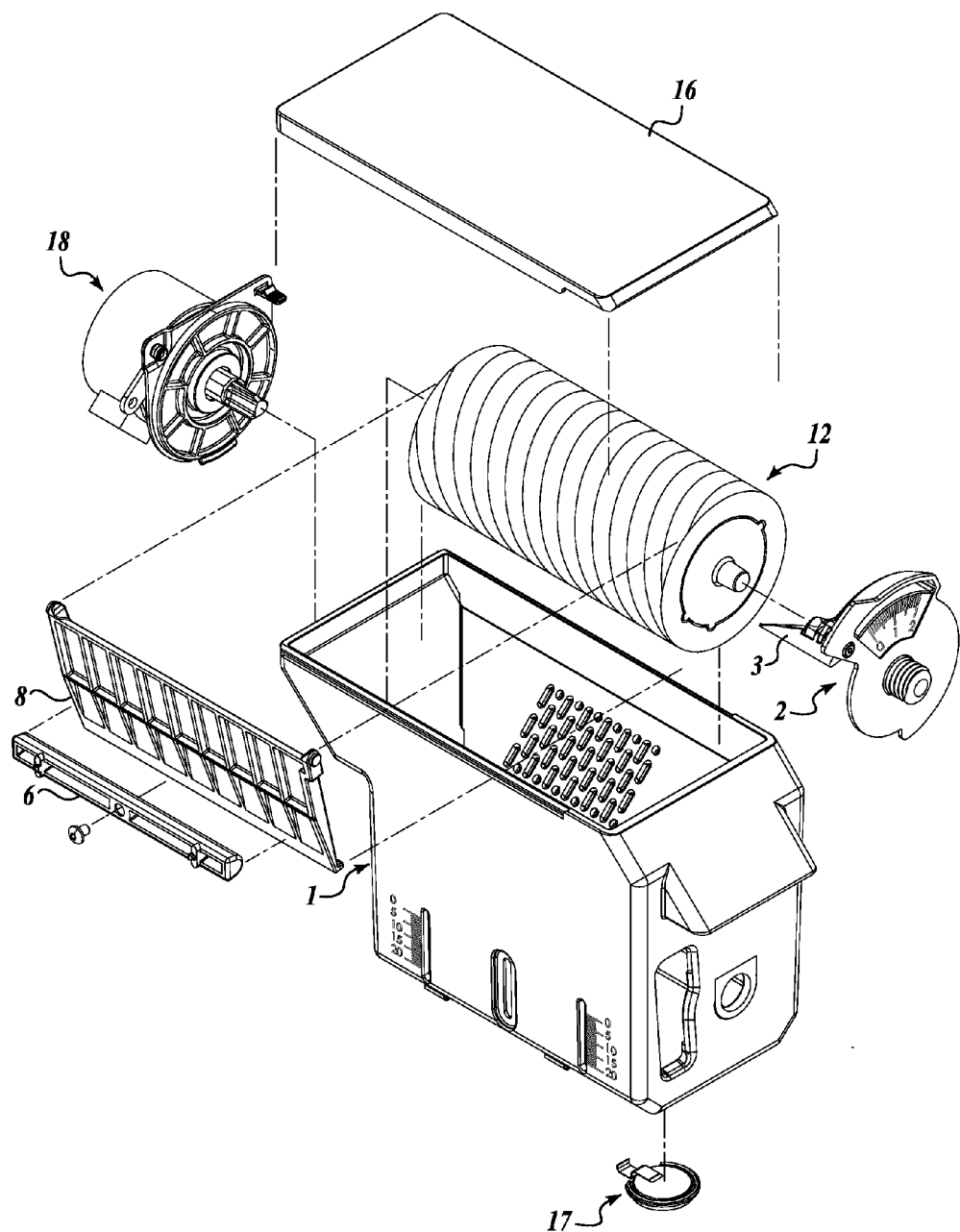
FIG. 2 is an exploded isometric view of the exemplary canister of FIG. 1A.

FIG. 1A is a top isometric view of an exemplary canister 90 for use with embodiments of the present disclosure. FIG. 1B is a bottom isometric view of the exemplary canister 90 of FIG. 1A. FIG. 2 is an exploded isometric view of the exemplary canister 90 of FIG. 1A. As shown in FIGS. 1A, 1B, and 2, the canister 90 includes a canister housing 1 that holds configurable parts and a quantity of a medication. In many embodiments, a medication is in the form of a pill, a tablet, and/or the like, and may be used to administer a drug to a patient. In some embodiments, the medication may be in liquid form, in which case the canister 90 may contain configurable components suitable for storing and dispensing predetermined amounts of liquid. Though the canister 90 is particularly useful for dispensing medications, in some embodiments the canister 90 may be used to dispense something other than a medication, such as some pill-shaped non-medication item, pieces of candy, and/or the like.

Referring now to FIG. 2, the canister 90 includes a singulation blade assembly 2 an auger assembly 12 to feed medication along a configurable sidewall 8 through a pill drop opening 18 (see FIG. 1A). The singulation blade assembly 2 includes a replaceable tip 3 which may be configured with a variety of settings. Similarly, the angle and positioning of the sidewall 8 may be changed via the positioning of a sidewall wedge 6. The canister housing 1 may be enclosed with a lid 16. The canister 90 may be coupled to a motor 18 which engages with the auger assembly 12. In some embodiments, the canister 90 is coupled to the motor 18 when the canister 90 is placed in a remote dispensing unit.

In some embodiments, information about the canister 90 may be stored on a canister data storage device 17. The canister data storage device 17 may comprise an RFID tag; a flash memory; an EEPROM in an iButton® accessible via a 1-Wire® serial communication bus such as those provided by Maxim Integrated Products, Inc; and/or the like.

In addition to settings that determine the physical configuration of the canister 90, other configuration variables may also be associated with the canister 90. For example, a motor forward or reverse torque setting used to turn the auger assembly 12, a motor speed for turning the auger assembly 12, a number of rotations of the auger assembly 12 or motor for dispensing a single piece of medication, an un-jam sequence for clearing jams in the canister 90, an auger reverse delay time, and/or the like may also be associated with the canister 90 to accurately dispense medication from the canister 90.

As the canister 90 illustrated in the figure has a number of configurable features, the canister 90 is particularly suitable for the discussion contained herein. However, the canister 90 shown and described is exemplary only, and one of ordinary skill in the art will appreciate that other configurable canisters may be used without departing from the scope of the present disclosure.

Figure 3:
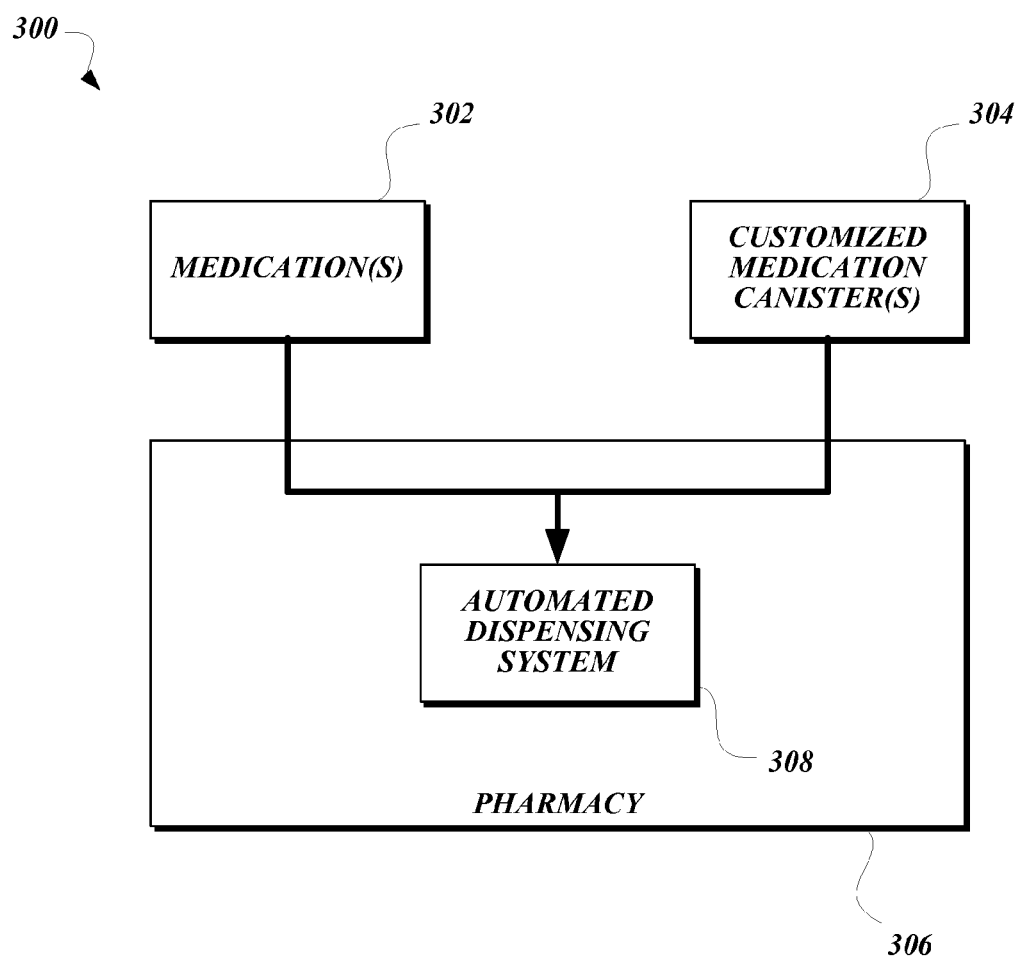
FIG. 3 is a block diagram that illustrates, at a high level, an embodiment of a workflow according to various aspects of the present disclosure.

FIG. 3 is a block diagram that illustrates, at a high level, an embodiment of a workflow 300 according to various aspects of the present disclosure. A pharmacy 306 is operated by an acute care facility, a long-term care facility, a correctional facility, public medical clinics, rural medical clinics, reservation medical clinics, and/or any other entity that dispenses medications. The pharmacy 306 utilizes an automated dispensing system 308 to dispense medications for administration to patients without requiring manual identification and/or counting of medications. For each of one or more medications 302 that are provided by pharmaceutical companies and/or the like, the pharmacy 306 obtains at least one customized medication canister 304 (which may or may not include a canister such as the canister 90 described above) configured to dispense the medication. The pharmacy 306 then fills the canister 304 with the medication 302 and uses the automated dispensing system 308 to dispense the medication 302 from the canister 304.

As each medication 302 may require a unique configuration of the configurable components of the canister 304, embodiments of the present disclosure provide systems and methods for providing the configuration settings for a given medication. In general, when a new medication is developed, canister configuration settings are determined that will cause a canister to correctly dispense the medication, and are stored in a centralized data repository. The canister configuration settings may be determined by the pharmacy 306, or an operator thereof, or may be determined by a third-party provider of canisters and/or canister data management services. Further, the canisters themselves may be built and configured by the pharmacy 306, or may be built and configured by a third-party provider of canisters. Advantageously, configurable canisters may be built from a supply of generic stock parts, which allows the party providing the canisters to build canisters for any past, present, or future medication without having to obtain newly manufactured parts specifically designed for the medication.

For ease of discussion, the canister lifecycle can be split into four major steps: design, in which canister configuration settings for a given medication are determined; build, in which a canister is built to dispense the given medication according to the determined canister configuration settings; fill, in which the built canister is filled with the medication; and dispense, in which the medication is dispensed from the canister. Each of these steps may be performed by different entities, by the same entity, or any combination of entities. Details of this process will be discussed further below.

Figure 4:
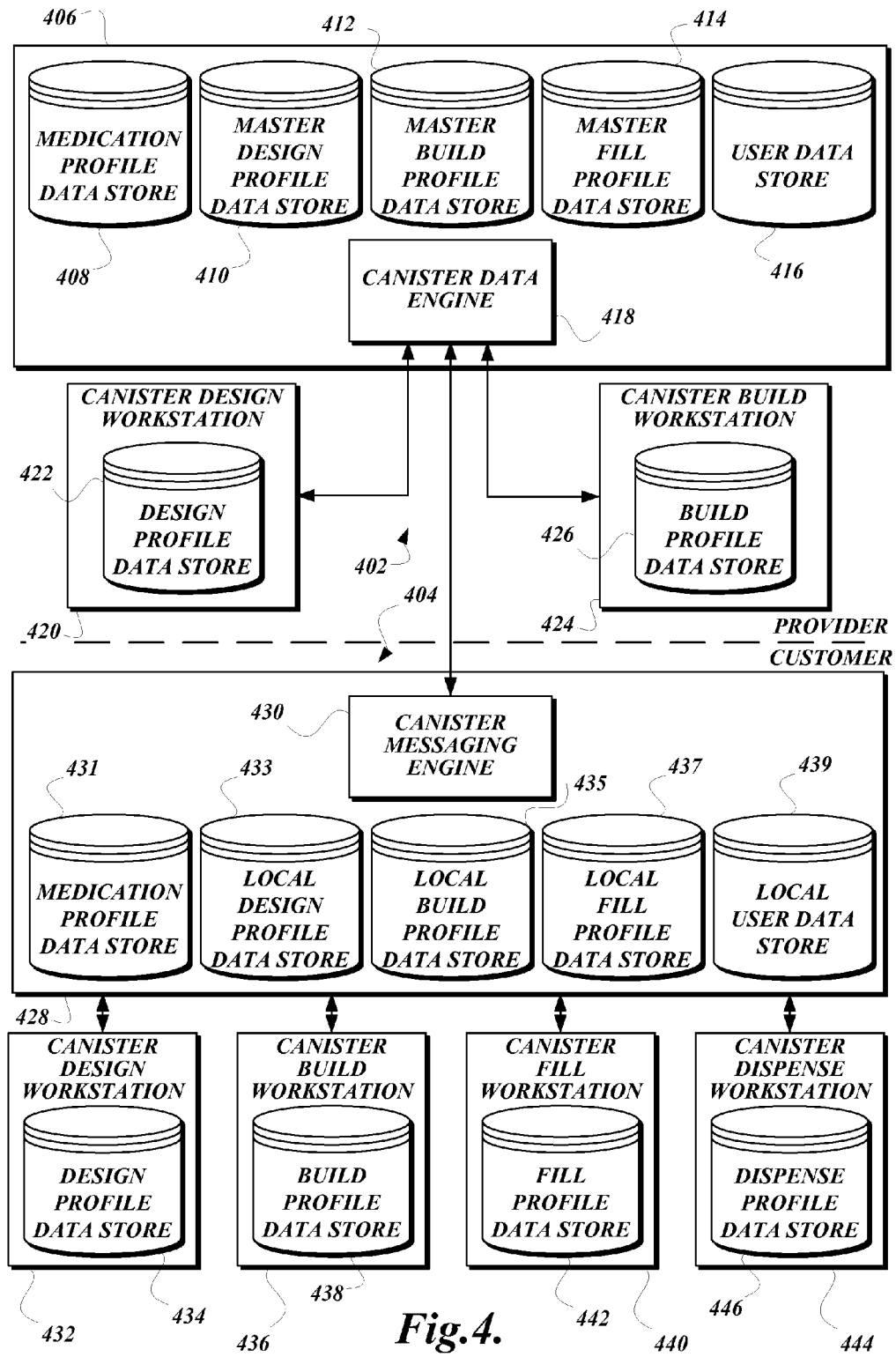
FIG. 4 is a block diagram that illustrates an exemplary embodiment of a system for managing canister data throughout the canister lifecycle, according to various aspects of the present disclosure.
Figure 5A:
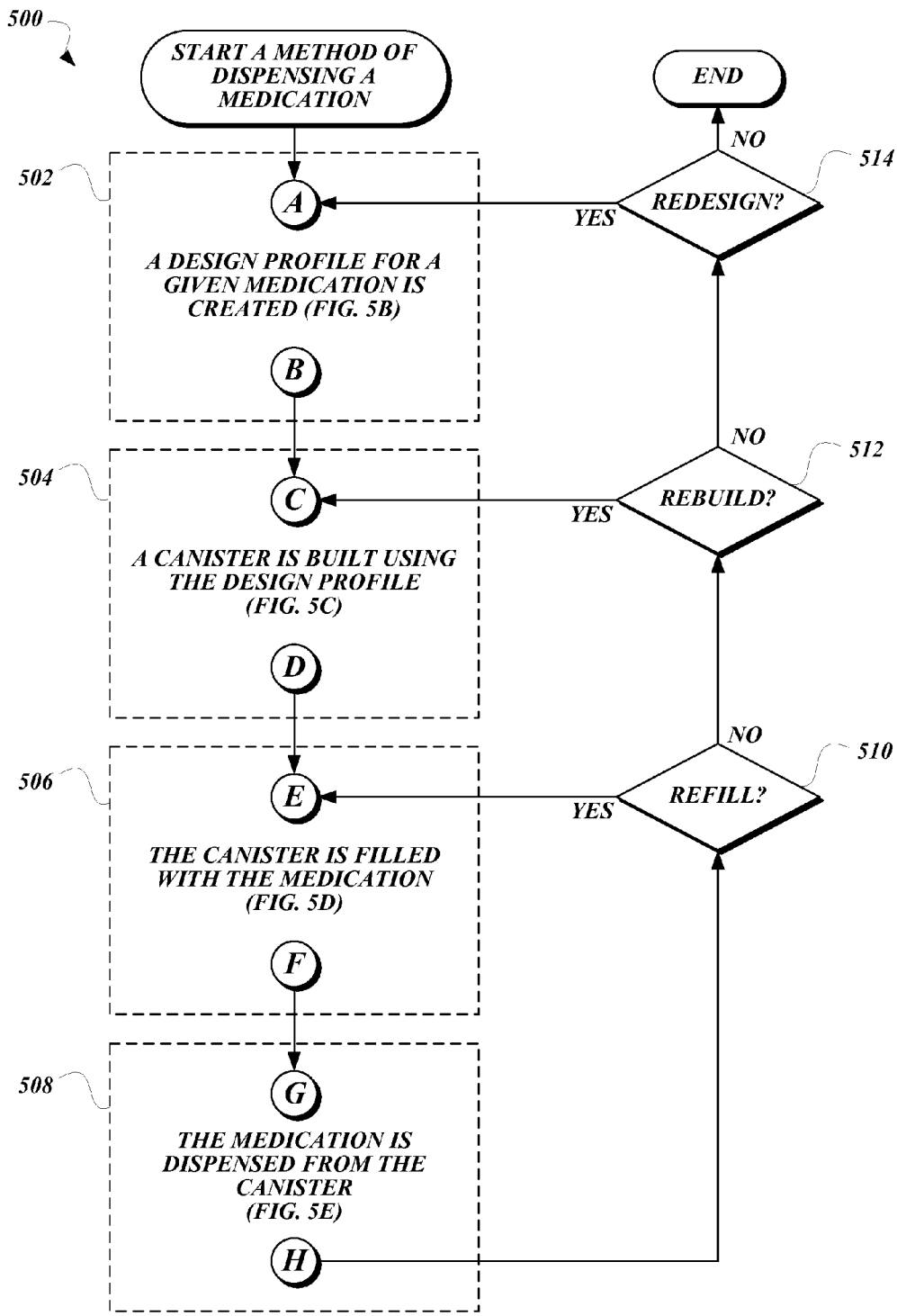
FIGS. 5A-5E illustrate an exemplary embodiment of a method of dispensing a medication according to various aspects of the present disclosure.
Figure 5B:
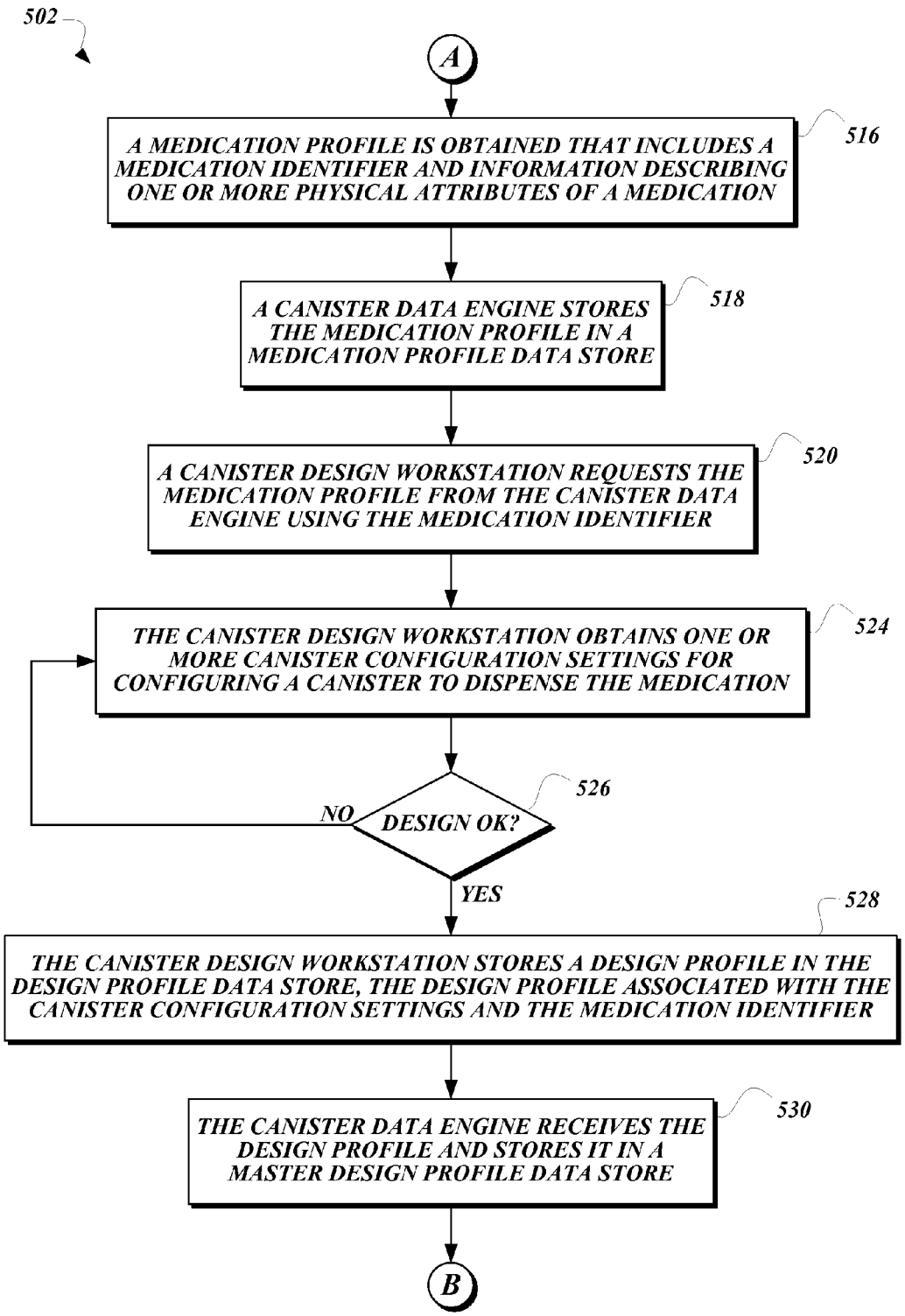
Figure 5C:
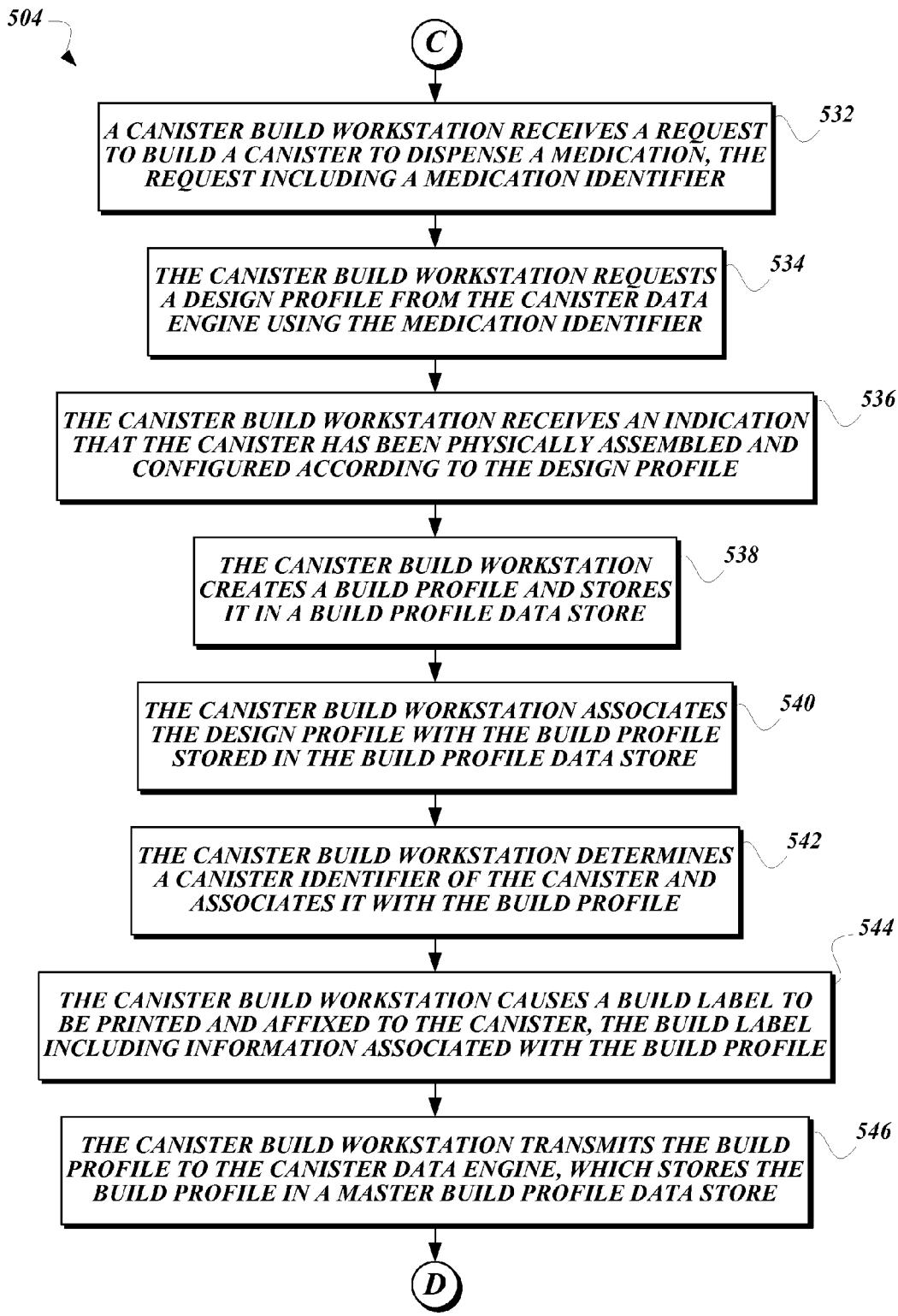
Figure 5D:
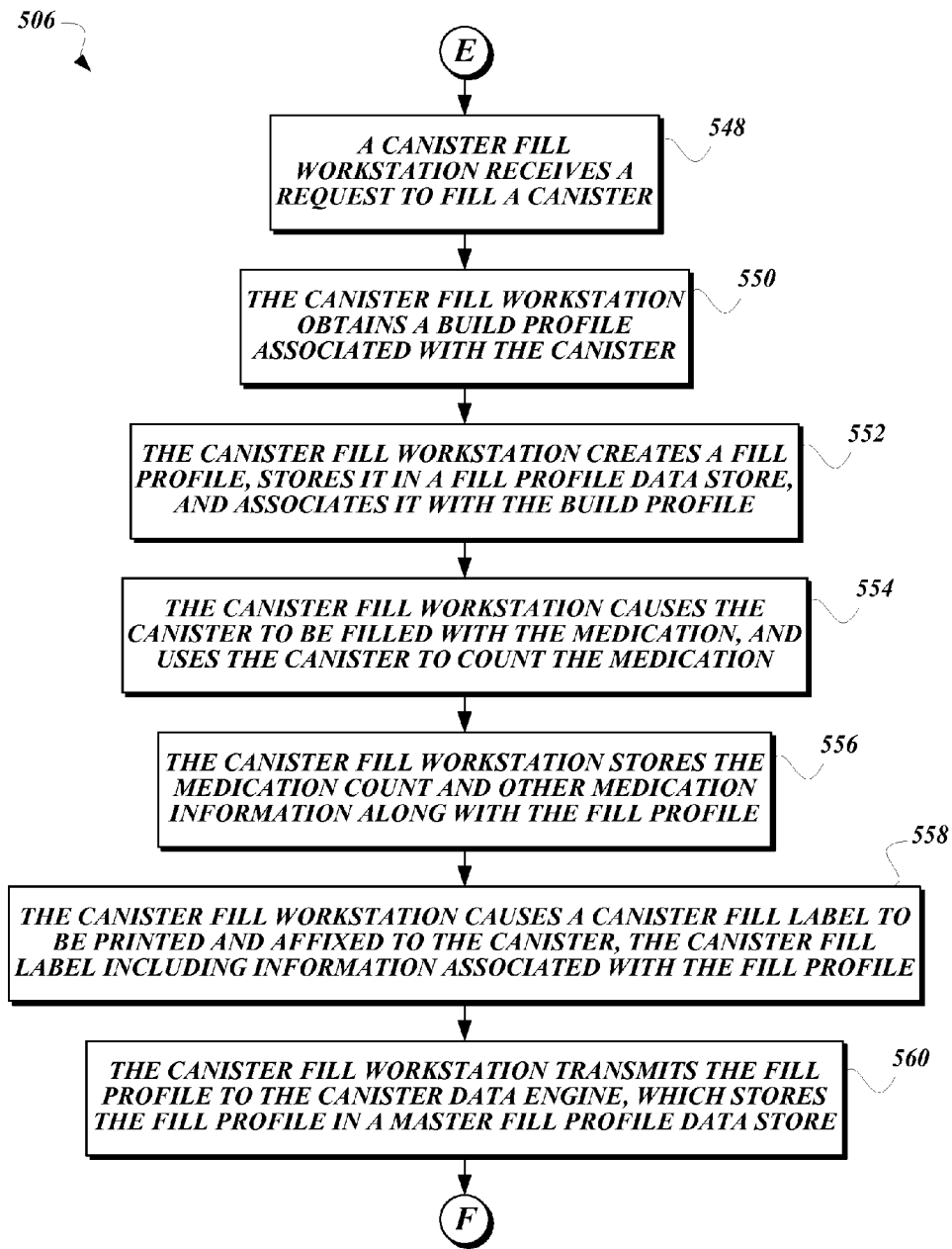
Figure 5E:
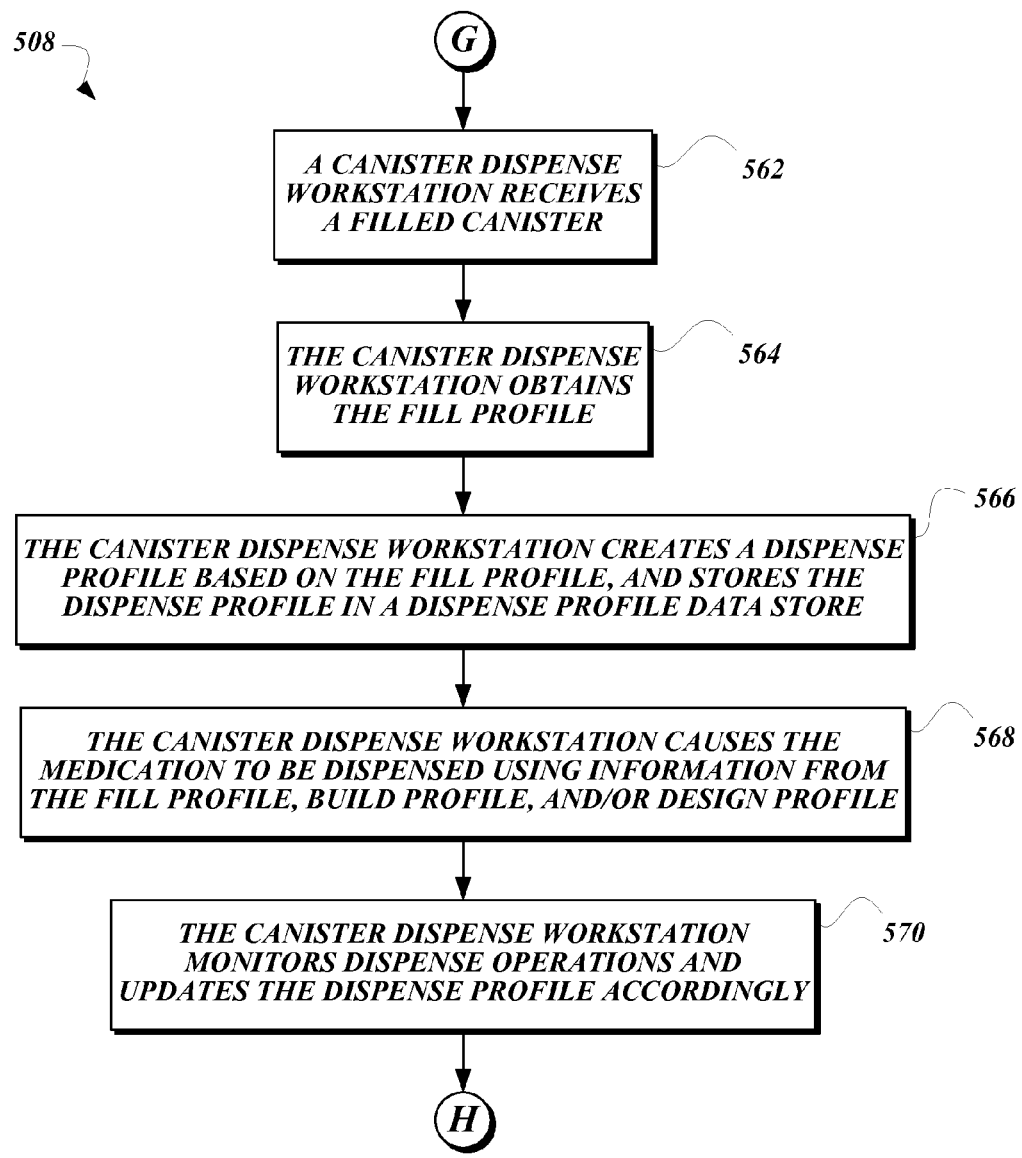

FIG. 4 is a block diagram that illustrates an exemplary embodiment of a system for managing canister data throughout the canister lifecycle, according to various aspects of the present disclosure. The illustration is divided into elements hosted by a canister provider 402 and elements hosted by a canister customer 404. The canister customer 404 may include a health care providing entity as discussed above, and at least includes an entity that will eventually use the canister to dispense medication. In some embodiments, the canister provider 402 may be an entity that manufactures canister components for assembly into configured canisters.

The canister provider 402 provides a centralized canister management system 406. The canister management system 406 stores canister configuration information, as discussed further below, and federates the configuration information to one or more customers 404 as requested. In some embodiments, the canister management system 406 makes canister configuration information available to more than one customer 404, but segregates said information such that access to information unique to a first customer is only provided to the first customer and not a second customer, though the second customer is provided with access to information unique to the second customer and to information common to the first customer and the second customer.

The canister management system 406 includes a medication profile data store 408. The medication profile data store 408 may store information describing a plurality of medications. Each medication is associated in the medication profile data store 408 with a unique identifier, such as a National Drug Code (NDC) (or a unique portion thereof), a unique identifier generated by the data store, and/or the like. The medication profile data store 408 may also store one or more attributes of the medication, including, but not limited to, a trade name, a United States Adopted Name, an International Nonproprietary Name, a shape, one or more dimensions, composition information, coloring information, and/or the like.

The canister management system 406 also includes a master design profile data store 410, a master build profile data store 412, and a master fill profile data store 414. These data stores may store information related to various steps of the canister build process. For example, the master design profile data store 410 is configured to store one or more design profiles, which are created during the design portion of the canister build process. A design profile may contain information usable to build a canister configured for a given medication. The design profile may include a unique identifier of a medication, which may serve to associate the design profile with a medication profile. The design profile may include a separate unique identifier for identifying the design profile, or the design profile may be uniquely identified by the unique identifier of the medication. The design profile may include configuration information for physical characteristics of the canister, such as a selected screw feed, a selected singulation blade tip, a singulation blade tip configuration setting, a selected sidewall type, and/or the like. The design profile may also include operational configuration information, such as a motor torque setting for operating the auger, a motor speed setting for operating the auger, a number of motor rotations for dispensing the medication, a set of operations usable for clearing jams, and/or the like.

The master build profile data store 412 is configured to store one or more build profiles, which are created during the build portion of the canister build process. The build portion of the canister build process is the point when a canister is physically assembled according to the attributes indicated in a design profile associated with a medication profile of a desired medication. The build profile includes a unique identifier such as a GUID and/or the like for identifying the canister. The build profile may include information from the medication profile and/or the design profile, or may simply include the medication identifier and/or the separate unique identifier of the design profile so that information may be retrieved from the associated profiles as desired. The build profile may also include information related to the build process itself, such as a name or other identifier of a technician who built the canister, a build date of the canister, and/or the like. As a nonlimiting example, the build profile may include one or more of the above-described identifiers and information associated with the following fields: a medication name; a medication strength; a medication type or unit such as tablet, gelcap, and/or the like; a medication NDC, a name of the technician who built the canister, a build date, an auger assembly selection; a singulation blade selection; a singulation blade setting; a side wall type selection; a blade tip angle; a medication bounce factor; a motor forward torque; a motor reverse torque; an auger reverse delay time; and a motor steps or revolutions setting.

The master fill profile data store 414 is configured to store one or more fill profiles, which are created during the fill portion of the canister build process. The fill portion of the canister build process is the point when the configured canister is filled with the medication. Though earlier portions of the canister build process may be performed by a canister provider, in some embodiments, the fill portion of the canister build process is performed by a pharmacy, as the handling of prescription medications may be involved. The fill profile may include the unique identifier of the build profile to reference information from the build profile, and/or may include information copied from the build profile. The fill profile may also include the medication identifier to reference information from the medication profile, and/or may include information copied from the medication profile. The fill profile may also include information related to the actual medication used to fill the canister and/or the act of filling the canister. As a nonlimiting example, the fill profile may include one or more of the above-described identifiers and information associated with the following fields: a medication name; a medication strength; a medication type or unit such as tablet, gelcap, and/or the like; a medication NDC, a medication mnemonic; a pack alone identifier; a medication color; a medication shape; a description of medication special markings; a medication manufacturer; a medication expiration date; a canister fill date; a medication lot number; a medication quantity or count; an identifier of a pharmacy technician who filled the canister; an identifier of a responsible pharmacist; a medication bounce factor; a motor forward torque; a motor reverse torque; and auger reverse delay time; and a motor steps or revolutions setting.

The canister management system 406 may also include a user data store 416. The user data store 416 includes user login information such as user identifiers, password information, and/or the like. The user data store 416 may also store a number of roles for each user, which define actions which the associated user is allowed to perform within the overall system. In some embodiments, the user data store 416 may not contain records for all end users of workstations, but may instead include authentication information for an intermediary canister messaging system 428, as described further below.

The canister management system 406 also includes a canister data engine 418. The canister data engine 418 may provide the interface and/or logic for interacting with the various data stores within the canister management system 406. In some embodiments, the interface provided by the canister data engine 418 may include a web site or some other graphical user interface to be accessed by users. In some embodiments, the interface may include a web service or other application programming interface (API) to be programmatically accessed by client applications executing on workstations or executing locally.

As stated above, the canister management system 406 may act as a centralized repository, and may federate data to other locations as needed. For example, different steps in the canister build process may be performed at task-specific workstations. As illustrated, the canister provider 402 also operates a canister design workstation 420 and a canister build workstation 424. In one embodiment, the canister design workstation 420 may be a computing device executing an application that allows a technician to create, edit, and otherwise manage design profiles. In a typical example, upon obtaining a new medication, a technician using the canister design workstation 420 may create a new design profile, and may edit the design profile while testing particular settings for the new medication. The design profile may be stored locally on the canister design workstation 420 in a design profile data store 422 at least until changes to the design profile are considered complete. The design profile may then be transmitted to the canister data engine 418, which saves the design profile to the master design profile data store 410. Likewise, the canister build workstation 424 may be a computing device executing an application that helps a technician build a canister based on a design profile. The canister build workstation 424 may retrieve the design profile from the master design profile data store 410 via the canister data engine 418. In one embodiment, the canister build workstation 424 displays information and/or instructions associated with the design profile, and may guide the technician through the build process for building a canister for a desired medication. Once the canister build is complete, a build profile may be stored in the build profile data store 426, which may then be transmitted to the canister data engine 418 as appropriate.

Data federation is not limited to a single entity such as the canister provider 402. Instead, in some embodiments, data may be federated to any number of business entities, through the use of a canister messaging system 428, such as the one illustrated as being associated with a customer 404. The canister messaging system 428 communicates directly with the canister data engine 418 of the canister management system 406 using a canister messaging engine 430, and acts as an intermediary for various function-specific workstations operated by the customer 404. For example, the customer 404 may operate a canister design workstation 432 and a canister build workstation 436, similar to the ones discussed above that were operated by the canister provider 402. The customer 404 may also operate a canister fill workstation 440 and/or a canister dispense workstation 444. The canister fill workstation 440 may be operated within a pharmacy or otherwise under the control of a pharmacist, as the canister fill operation may be associated with the handling of controlled substances. The canister dispense workstation 444 may be operated within a care facility as discussed above, and may be associated with or incorporated within a dispensing system that utilizes the canister to dispense the medication.

Each of the workstations includes a local data store, such as the illustrated design profile data store 434, build profile data store 438, fill profile data store 442, and dispense profile data store 446. These data stores are used for local profile creation and storage, similar to the discussion above with respect to the workstations operated by the canister provider 402. These data stores may also store data generated elsewhere and retrieved from the canister data engine 418 or the canister messaging system 428.

The canister messaging system 428 receives updated profiles from the workstations, and stores them in the appropriate local stores, such as a medication profile data store 431, a local design profile data store 433, a local build profile data store 435, and a local fill profile data store 437. The canister messaging system 428 may also include a local user data store 439 which stores information the canister messaging system 428 may use to manage access to various information and services.

The canister messaging engine 430 transmits the created or updated profiles from the local stores to the canister data engine 418 for storage in the master profile stores. The canister messaging system 428 also receives requests from the workstations for profile information. If the canister messaging system 428 has not stored the requested information in one of its associated data stores, the canister messaging engine 430 obtains the requested profile information from the canister data engine 418, which retrieves the requested profile information from the appropriate data store. The data federation communication between the workstations, the canister messaging system 428, and the canister management system 406 will be discussed further below.

In some embodiments, the canister messaging system 428 is also configured to pass messages relating to information other than data federation. For example, in some embodiments, the canister messaging system 428 enables a client application to subscribe to messages of a particular type. These messages may be published by any workstation or system in the data federation topology, and likewise may be subscribed to by an application at any point in the data federation topology. A record of each subscription may be stored by the canister messaging system 428 in an appropriate location, such as in the local user data store 439. Two examples of message types may be log messages and system information messages. Log messages may include pertinent event information that a client application would like to publish to other client applications. System information messages may contain information related to hardware or firmware components of a particular device within the system, such as a remote dispensing unit, a component of a canister, and/or the like. These message subscriptions may allow, for example, a client application associated with a canister fill workstation to be notified of an incoming empty canister to be filled so that an appropriate medication may be ordered and obtained in time for the canister to be filled in an efficient manner. As another example, the message subscriptions may allow troubleshooting log messages or system information messages to be relayed to the canister management system 406 for analysis by a maintenance technician.

Use of the canister messaging system 428 as an intermediary between the canister management system 406 and the workstations may provide additional benefits. For example, the canister messaging system 428 itself may be authenticated by the canister management system 406, and so the canister management system 406 does not have to process login information or otherwise authenticate end users of the workstations of the customer 404. This may allow the customer 404 greater flexibility in determining how to authenticate end users of its workstations. Further, federating data from the canister management system 406 to the canister messaging system 428 may provide lower latency and greater reliability in communication with each of the workstations, which may be geographically dispersed and/or only connected via unreliable network connections.

Federating data from the canister management system 406 may also allow a centralized entity to efficiently issue recalls or other notices relating to previously created canisters. For example, a problem may be found in an existing design profile. The canister management system 406 may place an indication in the design profile, as well as any build profile, fill profile, or dispense profile associated with the design profile, that the problem exists. The next time a workstation requests an associated profile from the canister management system 406, the indication will be found and the problem may be addressed. Similarly, the canister messaging system 428 may also store such indications, or may proactively transmit notifications to workstations connected thereto that problems exist in one or more profiles previously transmitted to the workstations.

The data federation described above also provides flexibility in terms of a canister supply chain. Each step in the canister build process may be performed by different business entities, and the data federation of the canister management system 406 makes any such split in responsibility transparent to entities performing other steps of the canister build process. For example, a first entity might operate the canister management system 406, and might manufacture and distribute parts that may be assembled into canisters. A second entity that provides canister design services might operate a canister design workstation 432, and may upload design profiles for new medications to the canister management system 406. A third entity may provide canister build services.

In response to receiving an order from a fourth entity for a canister for a given medication, the third entity may contact the canister data engine 418 to obtain the design profile created by the second entity, and may build and ship the requested canister to the fourth entity. The fourth entity, upon receiving the canister, may retrieve the design and build profile information from the canister data engine 418, and may send the canister to a pharmacy to be filled. The pharmacy may use the design and build profile information to fill the canister, and may create a fill profile for uploading to the canister data engine 418. The pharmacy may then send the filled canister to a care facility, where a canister dispense workstation 444 obtains the fill profile and uses it while dispensing the medication.

In some embodiments, some of the entities described above may be combined, or may be split into even further entities. Embodiments of the system described herein provide great flexibility with regard to this supply chain, while still providing all of the necessary information at every step. Further, information created by one entity may be reused by other entities, where appropriate. For example, a centralized entity may provide both the canister management system 406 and canister design services. However, a customer entity may prefer building their own canisters from parts instead of ordering pre-built canisters. The customer entity may use the canister management system 406 to obtain the design profile created by the centralized entity for a given medication during a build step conducted by the customer entity.

One of ordinary skill in the art will appreciate that various changes to the topology illustrated in FIG. 4 and the supply chain described above may be made without departing from the scope of the present disclosure. The canister management system 406 and each illustrated and described workstation may be provided by one or more computing devices, as described further below with respect to FIG. 6. One of skill in the art will recognize that the particular object boundaries illustrated in FIG. 4 are exemplary only, and that in some embodiments, computing devices illustrated in FIG. 4 as separate computing devices may be combined into a single computing device, and/or the functions of a single computing device illustrated in FIG. 4 may be performed by multiple computing devices.

FIGS. 5A-5E illustrate an exemplary embodiment of a method 500 of dispensing a medication according to various aspects of the present disclosure. From a start block (FIG. 5A), the method 500 proceeds to a set of method steps 502 defined between a start terminal ("terminal A") and a continuation terminal ("terminal B") in which a design profile for a given medication is created. This set of method steps 502 is similar to the design process described above.

From terminal A (FIG. 5B), the method 500 proceeds to block 516, where a medication profile is obtained that includes a medication identifier and information describing one or more physical attributes of a medication. Next, in block 518, a canister data engine 418 stores the medication profile in a medication profile data store 408.

In block 520, a canister design workstation 420 requests the medication profile from the canister data engine 418 using the medication identifier. Once the canister data engine 418 receives the request, the canister data engine 418 uses the medication identifier to retrieve the medication profile associated with the medication identifier from the medication profile data store. The canister data engine 418 then provides the medication profile to the requesting canister design workstation 420. As part of this process, the canister data engine 418 may check that the canister design workstation 420 submitting the request, or a user associated with the canister design workstation 420 submitting the request, has the right to retrieve the medication profile. For example, the canister data engine 418 may check the user data store 416 to ensure that the requester is associated with a role that allows access to data within the medication profile data store 408. In some embodiments, the canister design workstation 420 might not request a particular medication profile, but might instead request all new medication profiles that have not previously been downloaded, and/or all medication profiles that have changed since a previous request. In such an embodiment, the medication profile discussed below is one of the newly received or updated medication profiles.

The previous paragraph refers to the canister design workstation 420 illustrated in FIG. 4 that is operated by the canister provider 402, but as discussed above, the canister design workstation 420 may instead be operated by a customer 404, such as canister design workstation 432, or may be operated by any other entity. In such an embodiment, a canister messaging system 428 may act as an intermediary between the canister design workstation 432 and the canister messaging system 428. The canister messaging system 428 may receive the request for the medication profile, and may check the medication profile data store 431 for the requested information. If the information is not present in the medication profile data store 431, the canister messaging system 428 may pass the request along to the canister data engine 418. In some embodiments, the canister data engine 418 may authenticate that the canister messaging system 428 has the right to access information from the medication profile data store 408, and the canister messaging system 428 may separately authenticate the canister design workstation 432 or a user thereof.

Once the canister design workstation 420 receives the medication profile, the method 500 then proceeds to block 524, where the canister design workstation 420 obtains one or more canister configuration settings for configuring a canister to dispense the medication. As discussed above, the canister configuration settings may include physical settings such as a singulation blade, a sidewall angle, and so on, as well as other configuration variables such as a motor torque setting, a motor speed, an un-jam sequence, and so on. The method 500 then proceeds to a decision block 526, where a test is performed to determine whether the canister configuration settings are acceptable. This test may include acceptance testing of a prototype canister, in which a canister is built according to the canister configuration settings and is tested to determine whether the settings cause the canister to accurately and reliably dispense the medication.

If the answer to the test at decision block 526 is NO, the method 500 returns to block 524, where new canister configuration settings will be obtained. Otherwise, if the answer to the test at decision block 526 is YES, the method 500 proceeds to block 528, where the canister design workstation 420 stores a design profile in the design profile data store 420, the design profile associated with the canister configuration settings and the medication identifier. The design profile may include information from the medication profile, and/or may include the medication identifier to associate the design profile with the medication profile. In some embodiments, the design profile may include a unique design profile identifier to disambiguate multiple design profiles associated with a single medication identifier. In other embodiments, only one design profile may be allowed to exist for each medication identifier, and so the medication identifier may also be used to uniquely identify design profiles.

Next, in block 530, the canister data engine 418 receives the design profile and stores it in a master design profile data store 410. Once the design profile is stored in the master design profile data store 410, the method 500 proceeds to a continuation terminal ("terminal B"). In some embodiments, the design profile may be created by a customer canister design workstation 432. In such an embodiment, the design profile may be stored in the local design profile data store 433 instead of the master design profile data store 410. The canister messaging engine 430 may transmit the design profile to the canister data engine 418 upon request, at predetermined intervals, and/or the like.

From terminal B (FIG. 5A), the method 500 proceeds to a set of method steps 504 defined between a start terminal ("terminal C") and a continuation terminal ("terminal D") in which a canister is built using the design profile. This set of method steps 504 is similar to the build process described above. Though this set of method steps 504 is described for ease of discussion as following the set of method steps 502 in which the design profile is created, in some embodiments, the set of method steps 504 may stand alone, in that the design profile used in the set of method steps 504 may have been created by any method.

From terminal C (FIG. 5C), the method 500 proceeds to block 532, where a canister build workstation 424 receives a request to build a canister to dispense a medication, the request including a medication identifier. Similar to the discussion above with respect to the canister design workstation 420, the canister build workstation 424 may be a workstation operated by a canister provider 402, a workstation 436 operated by a customer, or a workstation operated by any other entity. As discussed above, some embodiments may include a canister messaging system 428 between the canister build workstation 436 and the canister data engine 418, such that the canister messaging system 428 is responsible for relaying information to and from the canister data engine 418, as well as caching information stored in the canister management system 406 for servicing requests by workstations. Also similar to the discussion above, the canister data engine 418 may authenticate the canister build workstation 424 or a user thereof before allowing access to data, and/or may authenticate the canister messaging system 428 which may then authenticate the canister build workstation 436 or a user thereof.

The method 500 then proceeds to block 534, where the canister build workstation requests a design profile from the canister data engine 418 using the medication identifier. As the medication identifier is unique, and is associated with the design profile as well as the medication profile, providing the medication identifier is sufficient, in some embodiments, for the canister data engine 418 to retrieve the appropriate design profile from the master design profile data store 410. In some embodiments, multiple design profiles may be stored in the master design profile data store 410 in association with a given medication identifier such as, for example, to create canisters usable with different dispensing systems, and/or the like. The request to the canister data engine 418 may include further information to uniquely identify an appropriate design profile, such as an intended dispensing system, and/or the like. Alternatively, the canister data engine 418 may retrieve all design profiles associated with the medication identifier, thus allowing the canister build workstation 424 to choose a design profile to use. As discussed above, the data requested from the canister data engine 418 may instead be requested from the canister messaging system 428.

Once the canister is physically assembled (which may be performed by a technician, a robot, an assembly line, or any other suitable method), the method 500 proceeds to block 536, where the canister build workstation 424 receives an indication that the canister has been physically assembled and configured according to the design profile. In block 538, the canister build workstation 424 creates a build profile and stores it in a build profile data store 426. Upon creation, the build profile may include a default set of build profile information. In block 540, the canister build workstation associates the design profile with the build profile stored in the build profile data store 426, such as by storing the medication identifier, the unique design profile identifier, or other information from the design profile in the build profile. Similar to the discussion above with respect to the design profile, the build profile may also include information copied from the medication profile and/or the build profile, or may include the medication identifier so that related information may be retrieved from the medication profile and/or the design profile associated with the medication identifier.

Next, in block 542, the canister build workstation 424 determines a canister identifier of the canister and associates it with the build profile. The canister identifier may be determined in any suitable way. For example, the canister build workstation 424 may generate a GUID that is then logically associated with the canister. As another example, one of the canister parts, such as the canister housing 1 or canister data storage device 17, may be associated with a unique identifier upon manufacture, and may have the unique identifier stamped, formed, stored or otherwise available thereon. In such an example, the canister identifier would be determined by obtaining the unique identifier of the canister part.

Next, in block 544, the canister build workstation 424 causes a build label to be printed and affixed to the canister, the build label including information associated with the build profile. In some embodiments, the canister build workstation 424 may include a label printer, or may be communicatively coupled to a label printer. Also, in some embodiments, a label printer of the canister build workstation 424 may be configured to automatically affix the label to the canister, while in other embodiments, the label may be manually affixed to the canister by a technician. The build label may contain the canister identifier, and may also contain further information from the build profile or other associated profiles, such as the medication identifier, the trade name, the physical configuration information (or a portion thereof), the operational configuration information (or a portion thereof), and/or the like.

Each of these pieces of information may be displayed on the build label in a human-readable format, such as an alphanumeric string and/or the like, and/or encoded in a machine-readable format, such as a bar code and/or the like. Each of these pieces of information may also be obtainable from the canister data engine 418, and the build label may provide a secondary data channel for communicating this information for reliability, convenience, or other reasons. In some embodiments, workstations may attempt to access the build profile information from various sources in a predetermined order. For example, a workstation may first attempt to obtain the build profile information from the canister messaging system 428 or the canister data engine 418 using a unique identifier of a canister part or of the build profile. If the build profile information is not available from one of these federation sources or the federation sources are not reachable, the workstation may obtain the build profile information from the build label.

In some embodiments, the federation sources may be a preferred source of information, as the data may be non-static. For example, canister design for a given medication may evolve as bugs of a particular design profile are discovered and addressed. If a canister is built and kept in inventory for a long time, the design profile for the associated medication may have changed by the time the canister is filled or the medication is dispensed. The information displayed on the build label will remain static, while the information available from the federation sources may be updated, and any critical differences between the current design profile and the design profile used to build the canister may be addressed when the canister is put into service from inventory by editing the build profile, associating the canister with the new design profile, invalidating the canister and causing it to be returned to an earlier stage in the build process, and/or the like.

In block 546, the canister build workstation 424 transmits the build profile to the canister data engine 418, which stores the build profile in a master build profile data store 412. In some embodiments, the build profile may be transmitted to the canister data engine 418 once it is completed. In other embodiments, updated or new build profiles stored in the build profile data store 426 may be transmitted to the canister data engine 418 after a predetermined amount of time has passed since the previous transmission, after a predetermined number of build profiles have been stored in the build profile data store 426, at a predetermined time of day, in response to a command received from a user by the canister build workstation 424, and/or by any other suitable method. In some embodiments, the build profile is transmitted instead to the canister messaging system 428, and is stored in the local build profile data store 435 until federated up to the canister data engine 418. The method 500 then proceeds to a continuation terminal ("terminal D").

From terminal D (FIG. 5A), the method 500 proceeds to a set of method steps 506 defined between a start terminal ("terminal E") and a continuation terminal ("terminal F") in which the canister is filled with the medication. This set of method steps 506 is similar to the fill process described above.

As discussed above with respect to the previously described sets of method steps, this set of method steps 506 may be performed after the previously described sets of method steps, or may be performed on its own once a built canister is obtained.

From terminal E (FIG. 5D), the method 500 proceeds to block 548, where a canister fill workstation 440 receives a request to fill a canister. In some embodiments, the request may be manually entered into the canister fill workstation 440 by a technician receiving an order for a canister filled with a particular medication. In other embodiments, the request may be received by the canister fill workstation 440 by scanning an indicator on an empty built canister. In still other embodiments, the request may be automatically generated by placing the canister on a device that automatically retrieves a unique identifier of a canister part, and that creates the request using the unique identifier. In some embodiments, the canister fill workstation 440 is operated by an entity that will be dispensing the medication. The canister fill workstation 440 may typically be associated with a pharmacy operated by the dispensing entity, though the pharmacy may or may not be located in the same location or facility at which the medication will be dispensed.

The method 500 proceeds to block 550, where the canister fill workstation 440 obtains a build profile associated with the canister. In some embodiments, the build profile may be obtained using the canister identifier. The canister identifier may be obtained by scanning a bar code or other machine-readable formatted indicator from the build label, by automatically retrieving the canister identifier from a canister part such as the canister data storage device 17, or by manual entry by a technician. The canister identifier may then be used by the canister fill workstation 440 to obtain the build profile via the canister messaging system 428.

If the canister messaging system 428 had previously obtained the build profile associated with the canister identifier and had not received a notification that the build profile had been updated, the canister messaging system 428 may provide the build profile from the local build profile data store 435. Otherwise, the canister messaging system 428 may use the canister identifier to obtain the build profile from the canister data engine 418, which retrieves the build profile from the master build profile data store 412. In some embodiments, the canister fill workstation 440 may obtain the build profile directly from the canister data engine 418 instead of using the canister messaging system 428. In some embodiments, the canister fill workstation 440 may also obtain the build profile, or a relevant portion thereof, from the build label to avoid requesting the information from the canister messaging system 428 or in cases when the canister messaging system 428 is not available.

Next, in block 552, the canister fill workstation 440 creates a fill profile, stores it in a fill profile data store 442, and associates it with the build profile. The fill profile may include a unique fill profile identifier which may serve to uniquely identify the particular fill profile. As a canister may be refilled multiple times (as discussed further below), the unique fill profile identifier helps to disambiguate multiple fill profiles that are associated with a single canister and/or build profile. In some embodiments, the fill profile includes the canister identifier for associating the build profile with the fill profile.

In block 554, the canister fill workstation 440 causes the canister to be filled with the medication, and uses the canister to count the medication. In some embodiments, the canister fill workstation 440 may display instructions to a technician that identify a medication with which to fill the canister. In some embodiments, a robot, assembly line, or other automated mechanism may be used to automatically fill the canister with the medication. The canister is filled with an appropriate amount of the medication, such as to a fill line indicated on the canister, to the top of the canister, with a remaining stock of the medication, and/or the like, though the medication is not counted before being placed in the canister. The automated dispensing mechanism of the canister is then activated to count the amount of medication that was placed in the canister. Once the count is performed, the counted medication is placed back in the canister. In some embodiments, the use of the canister to count the medication may be optional, such as in cases where the canister is filled from one or more medication sources having a known reliable count (e.g., a previously unopened 200-count bottle of medication is emptied into the canister). In such an embodiment, the count may be manually entered by a technician.

Next, in block 556, the canister fill workstation 440 stores the medication count and other medication information along with the fill profile. In block 558, the canister fill workstation 440 causes a canister fill label to be printed and affixed to the canister, the canister fill label including information associated with the fill profile. In some embodiments the canister fill workstation 440 may include a label printer, or may be communicatively coupled to a label printer. As discussed above with respect to the build label, the label printer associated with the canister fill workstation 440 may be configured to automatically affix the label to the filled canister, or the label may be manually affixed to the canister by a technician. The fill label may be used to seal the lid 16 to the housing 1, and may contain security features, such as signature fields to be signed by a pharmacist, fraud detection patterns, anti-tamper adhesives, and/or the like. The fill label may include the fill profile identifier, and may also contain further information from the fill profile, the build profile, or the design profile, in human-readable format and/or machine-readable format, as discussed above with respect to the build label. In some embodiments, the fill label may include information such as the trade name of the medication, the count of the medication, the name of the responsible pharmacist, a fill date, an expiration date, and/or the like. The fill profile and label may also include information about the use of the filled canister, such as a delivery location to which the filled canister should be delivered, and/or the like.

In block 560, the canister fill workstation 440 transmits the fill profile to the canister data engine 418, which stores the fill profile in a master fill profile data store 414. In some embodiments, the canister fill workstation 440 may transmit the fill profile to the canister messaging system 428 instead, which stores the fill profile in the local fill profile data store 437. As fill profile information may generally only be useful or relevant to the entity filling the canister and/or dispensing the medication, in some embodiments, the canister messaging system 428 may not transmit the fill profile information to the canister data engine 418, but may instead merely store and manage the fill profile locally, and may federate the fill profile information to a canister dispense workstation 444 connecting to the canister messaging system 428 upon request. In some embodiments, the canister messaging system 428 may transmit the fill profile to the canister data engine 418 for backup storage, and the canister data engine 418 may not provide data federation services for the fill profile.

The method 500 then proceeds to a continuation terminal ("terminal F"). From terminal F (FIG. 5A), the method 500 proceeds to a set of method steps 508 defined between a start terminal ("terminal G") and a continuation terminal ("terminal H") wherein the medication is dispensed from the canister. This set of method steps 508 is similar to the dispense process described above. The set of method steps 508 may be performed after the previously described steps, or may be performed in isolation if the data consumed during the steps and a filled canister are made available by some other method. From terminal G (FIG. 5E), the method 500 proceeds to block 562, where a canister dispense workstation 444 receives a filled canister. As discussed above, the canister dispense workstation 444 may be located at a care facility, and may be associated with an automated dispensing system configured to actuate the canister mechanism to dispense the medication.

In block 564, the canister dispense workstation 444 obtains the fill profile. In some embodiments, the canister dispense workstation 444 may request the fill profile from the canister messaging system 428, which will check the local fill profile data store 437 for a copy of the fill profile. If a copy of the fill profile is stored in the local fill profile data store 437, the canister messaging system 428 will provide the copy of the fill profile to the canister dispense workstation 444 without requesting it from the canister data engine 418. If a copy of the fill profile is not stored in the local fill profile data store 437, the canister messaging system 428 may request the fill profile from the canister data engine 418, which will retrieve it from the master fill profile data store 414.

In some embodiments, requesting the fill profile may include obtaining the fill profile identifier in a machine-readable format or a human-readable format from the fill label, and requesting the fill profile using the fill profile identifier. In some embodiments, the fill profile may be obtained in a different way, such as by obtaining the build identifier from the build label, and requesting the most recent fill profile associated with the build identifier. In block 566, the canister dispense workstation 444 creates a dispense profile based on the fill profile, and stores the dispense profile in a dispense profile data store 446. The dispense profile may track information related to the dispensing of the medication, such as a remaining count, a running tally of dispense events, and/or the like. Upon creation, the dispense profile may include a remaining count that matches the count from the fill profile.

In block 568, the canister dispense workstation 444 causes the medication to be dispensed using information from the fill profile, build profile, and/or design profile. In some embodiments, the canister dispense workstation 444 uses the operational configuration information from the design profile to operate the canister mechanism to dispense the medication. As discussed above, this information may be copied from the design profile into the build profile or fill profile, or it may be obtained from the canister messaging system 428 or the canister data engine 418 using the fill profile identifier, build profile identifier, canister identifier, design profile identifier, or medication identifier to retrieve the appropriate data from the appropriate source.

In block 570, the canister dispense workstation 444 monitors dispense operations and updates the dispense profile accordingly. For example, upon each dispense operation, the canister dispense workstation 444 may add a dispense event record to the dispense profile, or may update the remaining count in the dispense profile.

In some embodiments, dispense profiles may not be used. Instead, the fill profile may include information relating to a current state of the filled canister after one or more dispense operations. In such an embodiment, the canister dispense workstation 444 may include a fill profile data store 442 instead of a dispense profile data store 446. One of ordinary skill in the art will recognize that the fill profile may be treated similarly to how the dispense profile was discussed above without departing from the scope of the invention. In some embodiments, dispense profiles (or a subset of the information contained therein) may be transmitted to the canister messaging system 428 or the canister data engine 418 for storage, either in one of the data stores illustrated in FIG. 4 or in a separate data store that is not illustrated in the drawing.

Once the remaining count reaches zero or the canister is otherwise determined to be empty, the method 500 proceeds to a continuation terminal ("terminal H"). From terminal H (FIG. 5A), the method 500 proceeds to a decision block 510, where a test is performed to determine whether the empty canister should be refilled. If there is a continuing need to dispense the medication for which the empty canister is configured, it may make sense to refill the canister instead of beginning the entire canister supply process over to rebuild a new canister. This may particularly be true in situations where the canisters are built by an entity other than the entity that fills the canisters or dispenses the medication, and therefore obtaining newly built canisters would require ordering them from the other entity, awaiting deliver, and so on. If it is determined that the empty canister should be refilled, the answer to the test at decision block 510 is YES, and the method 500 proceeds to terminal E, where the set of method steps 506 is performed again to refill the canister with the medication. In some embodiments, a new fill profile will be created. In other embodiments, the previous fill profile may be reused and updated with the new information.

If it is determined that the empty canister should not be refilled, the answer to the test at decision block 510 is NO, and the method 500 proceeds to a decision block 512, where a test is performed to determine whether the canister should be rebuilt. Even if there is not a continuing need for the particular canister build, the parts for the canister may be reused in other canisters, or the same parts may be reconfigured so that the canister may dispense a different medication. In some cases, an updated build profile may be available for the same medication, and the settings of the canister should therefore be changed before the canister is filled again. Accordingly, if it is determined that the canister should be rebuilt, the answer to the test at decision block 512 is YES, and the method 500 proceeds to terminal C, where the set of method steps 504 is performed again to rebuild the canister. In some embodiments, the previous build profile may be updated with information relating to the new build. In other embodiments, a new build profile may be created.

If it is determined that the canister should not be rebuilt, the answer to the test at decision block 512 is NO, and the method 500 proceeds to a decision block 514, where a test is performed to determine whether the canister should be redesigned. If the empty canister is not refilled and not rebuilt, the canister parts may still be useful in designing canisters for new medications. On the other hand, the canister parts may be damaged, worn out, or unsuitable for use with other medications due to regulations or contamination. If it is determined that the canister parts may be reused in a new design, the answer to the test at decision block 512 is YES, and the method 500 proceeds to terminal A, where the set of method steps 502 is performed again to create a new canister design using the canister parts. If it is determined that the canister should not be redesigned, the answer to the test at decision block 514 is NO, and the method 500 proceeds to an end block and terminates.

Figure 6:
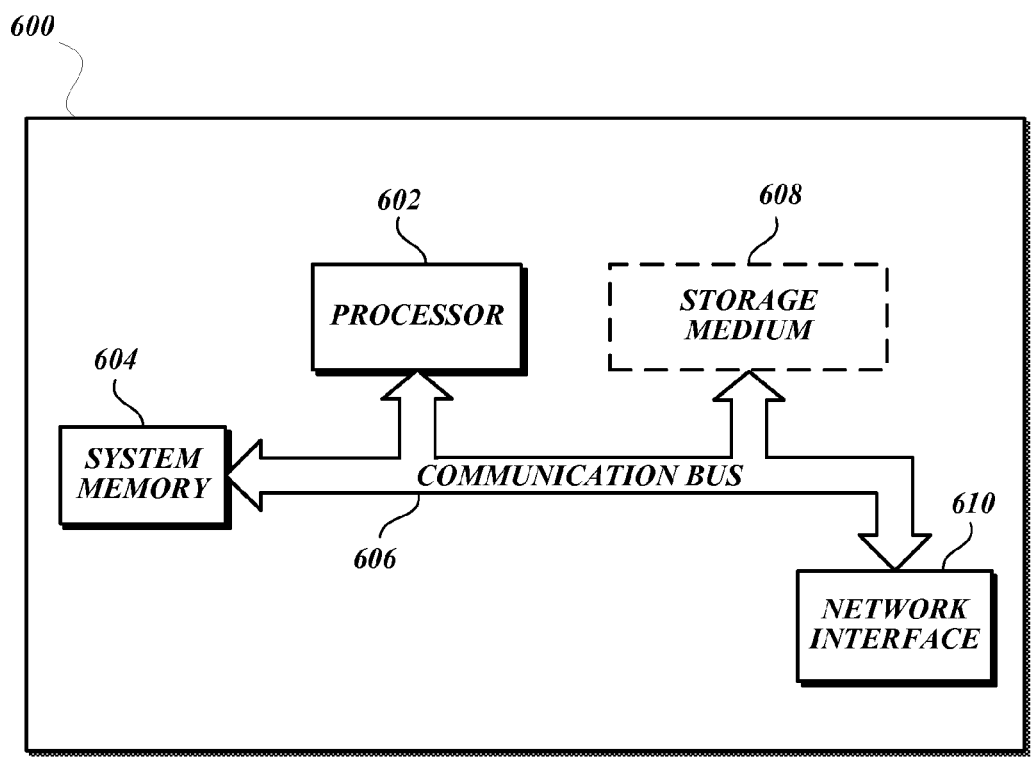
FIG. 6 illustrates aspects of an exemplary computing device appropriate for use with embodiments of the present disclosure.

FIG. 6 illustrates aspects of an exemplary computing device 600 appropriate for use with embodiments of the present disclosure. While FIG. 6 is described with reference to a computing device that is implemented as a device on a network, the description below is applicable to servers, personal computers, mobile phones, smart phones, embedded computing devices, and other devices that may be used to implement portions of embodiments of the present disclosure. Moreover, those of ordinary skill in the art and others will recognize that the computing device 600 may be any one of any number of currently available or yet to be developed devices.

In its most basic configuration, the computing device 600 includes at least one processor 602 and a system memory 604 connected by a communication bus 606. Depending on the exact configuration and type of device, the system memory 604 may be volatile or nonvolatile memory, such as read only memory ("ROM"), random access memory ("RAM"), EEPROM, flash memory, or similar memory technology. Those of ordinary skill in the art and others will recognize that system memory 604 typically stores data and/or program modules that are immediately accessible to and/or currently being operated on by the processor 602. In this regard, the processor 602 may serve as a computational center of the computing device 600 by supporting the execution of instructions.

As further illustrated in FIG. 6, the computing device 600 may include a network interface 610 comprising one or more components for communicating with other devices over a network. Embodiments of the present disclosure may access basic services that utilize the network interface 610 to perform communications using common network protocols. The network interface 610 may also include a wireless network interface configured to communicate via one or more wireless communication protocols.

In the exemplary embodiment depicted in FIG. 6, the computing device 600 also includes a storage medium 608. However, services may be accessed using a computing device that does not include means for persisting data to a local storage medium. Therefore, the storage medium 608 depicted in FIG. 6 is represented with a dashed line to indicate that the storage medium 608 is optional. In any event, the storage medium 608 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed packet switched network. However, any other suitable storage technique and/or device capable of quickly and reliably providing the stored data in response to queries may be used, and the computing device may be accessible locally instead of over a network, or may be accessible over some other type of suitable network or provided as a cloud-based service. A data store may also include data stored in an organized manner on a storage medium 608.

As used herein, the term "computer-readable medium" includes volatile and non-volatile and removable and non-removable media implemented in any method or technology capable of storing information, such as computer readable instructions, data structures, program modules, or other data. In this regard, the system memory 604 and storage medium 608 depicted in FIG. 6 are merely examples of computer-readable media.

Suitable implementations of computing devices that include a processor 602, system memory 604, communication bus 606, storage medium 608, and network interface 610 are known and commercially available. For ease of illustration and because it is not important for an understanding of the claimed subject matter, FIG. 6 does not show some of the typical components of many computing devices. In this regard, the computing device 600 may include input devices, such as a keyboard, keypad, mouse, microphone, touch input device, touch screen, tablet, and/or the like. Such input devices may be coupled to the computing device 600 by wired or wireless connections including RF, infrared, serial, parallel, Bluetooth, USB, or other suitable connections protocols using wireless or physical connections. Similarly, the computing device 600 may also include output devices such as a display, speakers, printer, etc. Since these devices are well known in the art, they are not illustrated or described further herein.

In general, the word "engine" (used interchangeably with the word "application"), as used herein, refers to logic embodied in hardware or software instructions, which can be written in a programming language, such as C, C++, COBOL, JAVA™, PHP, Perl, HTML, CSS, JavaScript, VBScript, ASPX, Microsoft .NET™ languages such as C#, and/or the like. An engine may be compiled into executable programs or written in interpreted programming languages. Software engines or applications may be callable from other engines or from themselves. Generally, the engines or applications described herein refer to logical modules that can be merged with other engines or applications, or can be divided into sub-engines. The engines or applications can be stored in any type of computer-readable medium or computer storage device and be stored on and executed by one or more general purpose computers, thus creating a special purpose computer configured to provide the engine or application.

While illustrative embodiments have been illustrated and described, it will be appreciated that various changes can be made therein without departing from the spirit and scope of the invention, as claimed.

The embodiments of the invention in which an exclusive property or privilege is claimed are defined as follows:

1. A computer-readable medium having computer-executable instructions stored thereon that, if executed by one or more processors of a computing device, cause the computing device to perform actions for managing canister data, the actions comprising:
   storing a design profile that includes configuration settings usable to configure a canister to dispense a medication;
   storing a build profile that includes information associated with a canister built based on the design profile; and
   storing a fill profile that includes information associated with filling the canister with the medication.

2. The computer-readable medium of claim 1, wherein the actions further comprise storing a dispense profile that includes information associated with dispensing the medication from the canister.

3. The computer-readable medium of claim 2, wherein the actions further comprise receiving the dispense profile from a canister dispense workstation.

4. The computer-readable medium of claim 1, wherein the actions further comprise receiving the design profile from a canister design workstation.

5. The computer-readable medium of claim 1, wherein the actions further comprise:
   transmitting the design profile to a canister build workstation in response to a request containing a medication identifier associated with the design profile; and
   receiving the build profile from the canister build workstation.

6. The computer-readable medium of claim 1, wherein the actions further comprise:

transmitting the build profile to a canister fill workstation in response to a request containing a canister identifier associated with the build profile; and receiving the fill profile from the canister fill workstation.

7. The computer-readable medium of claim 1, wherein the actions further comprise receiving a request for a design profile, a build profile, or a fill profile from a canister messaging system that communicatively couples one or more canister workstations to the canister management system.

8. The computer-readable medium of claim 1, wherein the actions further comprise causing a build label to be printed and affixed to the canister, wherein the build label includes information from the build profile.

9. The computer-readable medium of claim 1, wherein the actions further comprise causing a fill label to be printed and affixed to the canister, wherein the fill label includes information from the fill profile.

10. A system, comprising:
a canister management system, including:
one or more master profile data stores; and
a canister data engine communicatively coupled to the plurality of master profile data stores;
a canister messaging system communicatively coupled to the canister management system, the canister messaging system including:
one or more local profile data stores; and
a canister messaging engine communicatively coupled to the canister data engine and the one or more local profile data stores; and
one or more canister workstations configured to:
request profile information associated with a canister from the canister data engine or the canister messaging engine; and
submit new profile information to the canister data engine or the canister messaging engine.

11. The system of claim 10, wherein the one or more canister workstations are further configured to:
determine that desired profile information associated with a canister is not available from either the canister data engine or the canister messaging engine; and
obtain the desired profile information from the canister.

12. The system of claim 11, wherein the desired profile information is obtainable from a label on the canister.

13. The system of claim 12, wherein the desired profile information is printed in a machine-readable format or a human-readable format on the label on the canister.

14. The system of claim 10, wherein the canister messaging engine is configured to:
receive a request from a canister workstation for profile information;
in response to determining that a local profile data store includes the requested information, transmitting the requested information to the canister workstation; and
in response to determining that no local profile data store includes the requested information, transmitting a request for the requested information to the canister data engine.

15. The system of claim 10, wherein the canister management system and the canister messaging system are operated by separate entities.

16. A method for dispensing a medication from a configurable canister, the method comprising:
determining one or more canister configuration settings suitable to configure a canister to dispense the medication;
storing the canister configuration settings in a design profile;
building a canister based on the design profile;
storing information related to the building of the canister in a build profile;
filling the canister with the medication;
storing information related to the filling of the canister in a fill profile; and
dispensing the medication using the canister.

17. The method of claim 16, further comprising affixing a label to the canister, the label including the canister configuration settings in a machine-readable format or a human-readable format.

18. The method of claim 17, further comprising transmitting the design profile to a canister data engine for storage in a master design profile data store, and wherein building the canister based on the design profile includes requesting the design profile from the canister data engine.

19. The method of claim 18, wherein dispensing the medication using the canister includes:
obtaining the canister configuration settings stored in the design profile associated with the canister; and
using the canister configuration settings to dispense the medication.

20. The method of claim 19, wherein obtaining the canister configuration settings comprises:
in response to detecting that the canister data engine is available, obtaining the canister configuration settings by requesting the design profile from the canister data engine; and
in response to detecting that the canister data engine is not available, obtaining the canister configuration settings from a label affixed to the canister.

* * * * *